Figure 1:
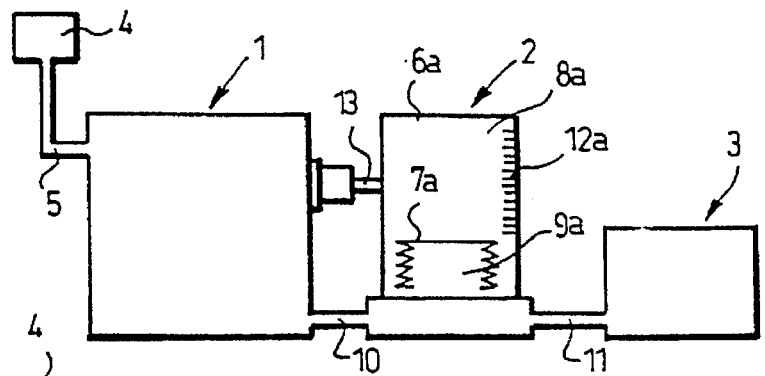

United States Patent [19]

Niemi et al.

[11] Patent Number: 5,647,352
[45] Date of Patent: Jul. 15, 1997

[54] ARRANGEMENT IN CONNECTION WITH A VENTILATOR

[75] Inventors: Hannes Niemi; Markku Hyvönen, both of Espoo, Finland

[73] Assignee: Instrumentarium Oy, Finland

[21] Appl. No.: 489,848

[22] Filed: Jun. 13, 1995

[30] Foreign Application Priority Data

Jun. 21, 1994 [FI] Finland .................................. 942990

[51] Int. Cl.$^6$ ................................................ A61M 16/00
[52] U.S. Cl. ........................... 128/204.28; 128/203.14; 128/204.18; 128/205.13; 128/205.23; 128/205.14
[58] Field of Search .................... 128/204.18, 204.21, 128/204.23, 204.28, 205.13, 205.14, 205.15, 205.23, 202.28, 202.29, 203.11, 203.14

[56] References Cited

U.S. PATENT DOCUMENTS

| | | | |
|---|---|---|---|
| 3,973,564 | 8/1976 | Carden | 128/205.14 |
| 4,096,858 | 6/1978 | Eyrick et al. | 128/145.6 |
| 4,256,100 | 3/1981 | Levy et al. | 128/205.24 |
| 4,603,691 | 8/1986 | Rusz | 128/205.15 |
| 4,637,385 | 1/1987 | Rusz | 128/205.14 |
| 4,978,335 | 12/1990 | Arthur, III | 604/67 |
| 5,315,989 | 5/1994 | Tobia | 128/205.24 |

FOREIGN PATENT DOCUMENTS

| | | | |
|---|---|---|---|
| 338518 | 10/1989 | European Pat. Off. . | |
| 8102677 | 10/1981 | WIPO | 128/204.21 |
| 88/10383 | 12/1988 | WIPO . | |

*Primary Examiner*—Vincent Millin
*Assistant Examiner*—V. Srivastava
*Attorney, Agent, or Firm*—Andrus, Sceales, Starke & Sawall

[57] ABSTRACT

An arrangement in connection with a ventilator that comprises a control unit, a bellows unit and a patient circuit, whereby the bellows unit is arranged to separate the control unit from the patient circuit and the control unit is arranged to implement control parameters characterizing lung ventilation. In order to eliminate human error, the arrangement is provided with an identification device that is arranged to identify the bellows unit to be used and to give notification on said bellows unit.

8 Claims, 1 Drawing Sheet

U.S. Patent  Jul. 15, 1997  5,647,352

ARRANGEMENT IN CONNECTION WITH A VENTILATOR

The invention relates to an arrangement in connection with a ventilator that comprises a control unit, a bellows unit and a patient circuit, whereby the bellows unit is arranged to separate the control unit from the patient circuit and the control unit is arranged to implement control parameters characterizing lung ventilation.

Arrangements of this kind are now well known in the field of hospital technology. A ventilator is a respirator apparatus with which a patient's lung ventilation is performed when the breathing activity of the patient is insufficient or totally obstructed.

The structure of ventilators using pressurized gas as a driving force can be divided into three parts: a control unit, a bellows unit and a patient circuit. The control unit implements control parameters characterizing lung ventilation, such as batch volume, respiratory frequency, the relation between inhalation and exhalation periods and inhalation pause. The bellows unit separates the ventilator's control unit that uses pressurized gas as a driving force and the patient circuit from each other. The bellows unit prevents the mixing of the patient's respiratory gas and the driving gas. The patient circuit builds separate routes for inhalation and exhalation gases to and from the patient and removes carbon dioxide from exhalation gases. The ventilator is described in more detail in U.S. Pat. No. 5,490,499, for instance.

One problem of prior art arrangements has been the manual selection of control parameters on the basis of each bellows unit in use. In practice, this means that bellows of different volume are used for child and adult patients. In ventilating child patients the pediatric bellows used is clearly smaller in volume than the bellows used for adult patients. When using said pediatric bellows with child patients, the compliance of the circuit is smaller, the dead volume can be minimized for children and the supplied volume can also be checked more accurately on a scale on the side of the bellows bottle. Because of patient safety, the parameters characterizing lung ventilation have to be selected with regard to the bellows unit in use and the size of the patient as was mentioned above. In the prior art arrangements the user of the apparatus has always been responsible for the suitability of the control parameters, for example, the volume settings for a child patient. The identification of the bellows has hitherto been only visual, that is, the user of the apparatus selects the bellows unit and then the control parameters manually. The drawback of this procedure is that there is always a possibility of human error or lapse of memory. It is to be noted that hospital staff very often has to act fast and under a lot of stress so that the possibility of human error grows.

It is an object of the invention to provide an arrangement with which the drawbacks of the prior art can be eliminated. This is achieved with the arrangement of the invention, which is characterized in that the arrangement is provided with an identification device that is arranged to identify the bellows unit to be used and to give notification on said bellows unit.

The advantage of the invention is primarily that by means of the invention faulty parameter settings caused by human error can be minimized. Automatic bellows identification makes it possible to transfer data to the apparatus without the user's involvement. The apparatus will set automatically the control parameter values for child patients, etc. This is essential because even if a smaller bellows as such restricts volume, for example, the normal volume used for adult patients is too large for small children. That would be closely equivalent to the volume of the entire child bellows. Furthermore, the apparatus can set a limit to overpressure and make all other settings suitable for child patients. A further advantage of the invention is its flexibility in practice as it can be applied very easily and there is no need to make any alterations to the bellows. This means that the invention can also be applied to the bellows in use now.

Figure 2:
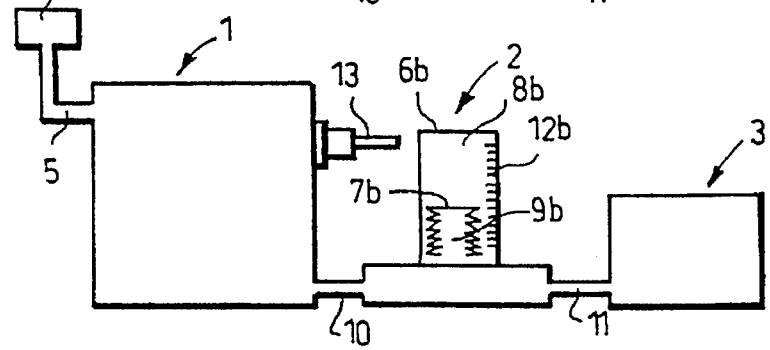
Figure 3:
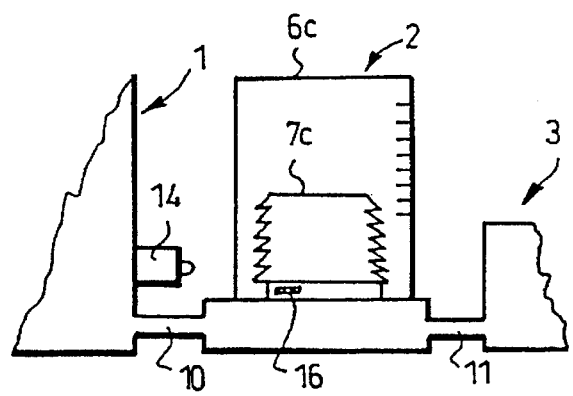
Figure 4:
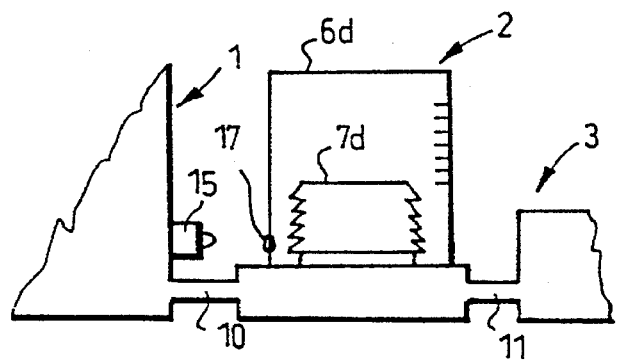
Figure 5:
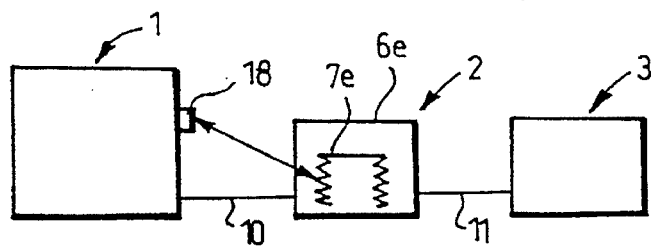

In the following, the invention will be described in more detail by means of a preferred embodiment illustrated in the accompanying drawing, in which FIG. 1 shows schematically an arrangement of the invention in a situation in which a bellows unit for an adult patient is used, FIG. 2 shows schematically the arrangement of FIG. 1 in a situation in which a bellows unit for a child patient is used, FIG. 3 shows schematically a second embodiment of the arrangement of the invention, FIG. 4 shows schematically a third embodiment of the arrangement of the invention and FIG. 5 shows a schematic diagram of a fourth embodiment of the arrangement of the invention.

FIG. 1 shows schematically an arrangement of the invention in connection with a ventilator. Reference numeral 1 denotes a control unit, reference numeral 2 a bellows unit and reference numeral 3 a patient circuit. In FIG. 1 reference numeral 4 denotes a source of driving gas from which gas to the control unit is conducted via a conduit 5.

The bellows unit consists of a container or a bellows bottle 6a and a bellows 7a inside it. There is a space 8a between the inner surface of the bellows bottle 6a and the bellows 7a. A bellows space 9a is inside the bellows 7a.

The control unit 1 conducts gas from the source of driving gas 4 via a conduit 10 in a required manner to the space 8a. When the pressure of the space 8a is higher than the pressure of gas in the bellows space 9a, the bellows 7a starts to compress. When driving gas flows to the space 8a, the bellows 7a compresses and gas in the bellows space 9a flows via a conduit 11 to the patient circuit 3. A scale 12a can be placed on the wall of the bellows bottle 6a for reading the volume of gas supplied to the patient circuit 3.

The above presentation of the basic operation of the ventilator represents fully conventional technology to a person skilled in the art, and thus these procedures will not be explained in more detail in this context. In this context a reference is made for example to U.S. Pat. No. 5,490,499 that describes the operation of the ventilator in more detail.

As was shown above, it is essential that the parameters regulating lung ventilation, that is volume etc., are correctly set with regard to the situation in question, that is, the correct values for a child patient, the correct values for an adult patient, etc. The above point is essential for patient safety.

In order to achieve bellows identification automatically, the essential idea of the invention is to provide the arrangement with an identification device 13 that is arranged to identify the bellows unit 2 to be used and to give notification on said bellows unit. The idea is that the apparatus identifies the bellows unit and notifies which bellows unit is switched on. Upon notification, the user can, for example, confirm the data so that the apparatus will make the required settings as programmed. At this stage the user can also feed some other special data required in the situation that will have an effect on ventilation. The identification device can also be arranged to transfer identification data directly to the control unit 1 that is arranged to indicate the correct control parameters on the basis of said identification data. The expression identifying the bellows unit to be used means that the identification device can automatically identify the volume of the bellows to be used, which the bellows will supply to the patient. In practice, the identification of the bellows unit can be done in many different ways. In the embodiment of FIG.

1 the identification device 13 contains a switching device that is arranged to identify the shape of the bellows bottle 6a in the bellows unit 2 in use. The switching device can for example be a simple switch that contacts the side of the bellows bottle 6a when it is installed. When the switch in contact with the bellows bottle turns from zero position to another position, a signal is sent to the control unit to notify that the bellows is meant for an adult. Upon receiving said identification data, the control unit 1 will adjust the parameters automatically to correct values. After receiving said identification data, the control unit will also notify, that is, indicate which parameters are selected. The user can then confirm the parameters before the arrangement makes all the required settings.

The essential idea of the invention will probably become more evident when studying FIGS. 1 and 2 simultaneously. FIG. 2 shows the arrangement of FIG. 1 when a bellows unit for a child patient is installed. The numerals used in FIG. 2 stand for the same reference points as in FIG. 1. In FIG. 2 reference numeral 6b denotes a bellows bottle and reference numeral 7b a bellows. Reference numeral 8b denotes a space between the bellows bottle 6b and the outer surface of the bellows 7b and reference numeral 9b denotes a bellows space. A scale placed on the wall of the bellows bottle 6b is denoted by reference numeral 12b.

As is shown in FIG. 2, the small bellows bottle 6b intended for a child patient is not in contact with the switching unit used as an identification unit 13, in which case the switching device will stay in zero position and the control unit 1 will be notified at the same time that the parameters have to be adjusted to be suitable for a child patient. The essential idea is that only the bellows bottle 6a for an adult patient turns the switching unit used as an identification unit 13 from zero position to another position so that the control unit 1 is notified in this situation only that the bellows unit is meant for an adult.

The identification device needs by no means be a device in contact with the bellows unit but it is also quite possible to use arrangements based on ultrasound, light, capacitive or magnetic processes, for instance.

The identification of the bellows unit can also be done in such a manner that the identification device identifies the bellows unit in use on the basis of an identification sign on the bellows unit. The identification sign can be arranged on the bellows or the bellows bottle. FIG. 3 shows an arrangement in which an identification sign 16 is arranged on the bellows. An identification device 14 identifies a bellows 7c by means of the identification sign 16. FIG. 4 shows an arrangement in which an identification sign 17 is arranged on the bellows bottle 6d. An identification device 15 identifies the bellows unit by means of the identification sign 17. Any suitable code or the like can be used as identification signs 16 and 17. The numerals used in FIGS. 3 and 4 stand for the same reference points as in FIGS. 1 and 2.

According to another essential idea of the invention it is quite possible that the identification device measures the volume of the bellows and determines the parameters on the basis of this measurement. FIG. 5 shows a schematic diagram of this arrangement. In this embodiment an identification device 18 measures the volume of a bellows 7e and transmits the measurement data to the control unit where the measurement data is compared to the reference data in memory to find the correct control parameters. The measurement of volume can be done in any known manner. The numerals used in FIG. 5 stand for the same reference points as in the embodiments above. This embodiment is of particular advantage in arrangements where the bellows is arranged to be suitable for a patient by restricting the upward expansion of the bellows with a suitable limiter, for instance. It is also possible to place a suitable identification sign on the device restricting the expansion of the bellows so that the arrangement will identify the bellows unit to be used, that is, the volume of the bellows to be used by means of said identification sign, etc.

The embodiments presented above are in no way intended to restrict the invention but the invention may be modified quite freely within the scope of the claims. Thus it is evident that the arrangement of the invention or its details need not necessarily be precisely as shown in the figures but other solutions can be used. For example, the control unit can be of any type, etc.

We claim:

1. Ventilator apparatus for ventilating patients having differing pulmonary characteristics, said apparatus comprising:

a patient circuit for providing a ventilating gas flow connection to a patient;

a selected one of a plurality of interchangeable, different bellows units coupled to said patient circuit, each of said bellows units having different ventilating gas controlling properties, the bellows unit coupled to said patient circuit being selected in accordance with the pulmonary characteristics of the patient undergoing ventilation;

control means for controlling the operation of said patient circuit and said selected one of said different bellows units; and identification means coupled to said control means for detecting which one of said plurality of different bellows units is coupled to said patient circuit and for providing an indication in accordance therewith.

2. The ventilator apparatus according to claim 1 wherein said identification means is further defined as providing a signal to said control means for causing said control means to operate said ventilator apparatus responsive to said signal.

3. The ventilator apparatus according to claim 1 wherein each of said bellows units has a different physical dimension and wherein said identification means detects the physical dimension of the bellows units coupled to said patient circuit.

4. The ventilator apparatus according to claim 3 wherein said identification means is capable of contacting said bellows unit to detect the physical dimension of the bellows units coupled to said patient circuit.

5. The ventilator apparatus according to claim 1 wherein each of said bellows units is provided with an identifier by which said identification means carries out its detection.

6. The ventilator apparatus according to claim 5 wherein each of said bellows units comprises an expandable bellows contained in a housing and wherein said identifier is located on said bellows.

7. The ventilator apparatus according to claim 5 wherein each of said bellows units comprises an expandable bellows contained in a housing and wherein said identifier is located on said housing.

8. The ventilator apparatus according to claim 1 wherein each of said bellows units includes a different sized expandable bellows, and wherein said identification means comprises means for detecting bellows size properties to detect which of said different bellows units is coupled to said patient circuit.

* * * * *